US008817085B2

(12) United States Patent
Hiltl et al.

(10) Patent No.: US 8,817,085 B2
(45) Date of Patent: Aug. 26, 2014

(54) CONTROL SYSTEM AND METHOD TO OPERATE AN OPERATING ROOM LAMP

(75) Inventors: Christoph Hiltl, Singen (DE); Omid Abri, Berlin (DE); Stephan Schrader, Kleinmachnow (DE)

(73) Assignee: Karl Storz GmbH & Co. KG (DE)

( * ) Notice: Subject to any disclaimer, the term of this patent is extended or adjusted under 35 U.S.C. 154(b) by 447 days.

(21) Appl. No.: 12/856,310

(22) Filed: Aug. 13, 2010

(65) Prior Publication Data

US 2011/0037840 A1     Feb. 17, 2011

(30) Foreign Application Priority Data

Aug. 14, 2009   (DE) .......................... 10 2009 037 316

(51) Int. Cl.
*H04N 7/18*     (2006.01)

(52) U.S. Cl.
USPC .......................................................... 348/61

(58) Field of Classification Search
USPC .......................................................... 348/61
See application file for complete search history.

(56) References Cited

U.S. PATENT DOCUMENTS

| | | | | |
|---|---|---|---|---|
| 4,084,149 | A * | 4/1978 | Driver et al. ...................... | 367/95 |
| 4,245,651 | A * | 1/1981 | Frost ............................... | 600/534 |
| 4,639,838 | A   | 1/1987 | Kato et al. | |
| 5,047,850 | A * | 9/1991 | Ishii et al. ...................... | 348/699 |
| 5,361,104 | A * | 11/1994 | Ohki ............................... | 348/699 |
| 5,363,303 | A * | 11/1994 | Kaneko et al. .................. | 701/45 |
| 5,434,927 | A * | 7/1995 | Brady et al. .................... | 382/104 |
| 5,550,726 | A * | 8/1996 | Hiromachi et al. ............. | 362/383 |
| 5,761,326 | A * | 6/1998 | Brady et al. .................... | 382/103 |
| 5,892,856 | A * | 4/1999 | Cooper et al. .................. | 382/291 |
| 6,290,645 | B1 * | 9/2001 | Goldfarb et al. ............... | 600/249 |
| 6,434,329 | B1 * | 8/2002 | Dube et al. ...................... | 396/14 |
| 6,504,610 | B1 * | 1/2003 | Bauer et al. .................... | 356/399 |
| 6,548,967 | B1 * | 4/2003 | Dowling et al. ............... | 315/318 |
| 6,785,578 | B2 * | 8/2004 | Johnson et al. ................ | 700/60 |

(Continued)

FOREIGN PATENT DOCUMENTS

| | | |
|---|---|---|
| CN | 201248169 Y | 5/2009 |
| DE | 1097382 B | 1/1961 |

(Continued)

OTHER PUBLICATIONS

Yang et al., Extraction of 2D Motion Trajectories and Its Application to Hand Gesture Recognition, 2002, IEEE, vol. 24, pp. 14.*

(Continued)

*Primary Examiner* — Sath V Perungavoor
*Assistant Examiner* — Peter D Le
(74) *Attorney, Agent, or Firm* — St. Onge Steward Johnston & Reens LLC (57) ABSTRACT

A control system to control an operating room lamp to generate light to illuminate a surgical site includes an image signal input to receive an image signal from a video camera to capture an image of a surgical site and a control signal output to emit to the operating room lamp a control signal to control at least either a direction or an intensity or a spectral characteristic of the light or a size or shape of the area illuminated by the light. The control system is configured to recognize a hand area of medical personnel and to generate the control signal depending on the image signal and to emit it to the control signal output.

15 Claims, 3 Drawing Sheets

(56) References Cited

U.S. PATENT DOCUMENTS

| | | | |
|---|---|---|---|
| 7,058,204 B2 * | 6/2006 | Hildreth et al. | 382/103 |
| 7,372,977 B2 * | 5/2008 | Fujimura et al. | 382/103 |
| 7,515,735 B2 * | 4/2009 | Miyamori | 382/103 |
| 7,555,142 B2 * | 6/2009 | Hildreth et al. | 382/103 |
| 7,565,295 B1 * | 7/2009 | Hernandez-Rebollar | 704/271 |
| 7,570,064 B2 * | 8/2009 | Roziere | 324/662 |
| 8,269,176 B2 * | 9/2012 | D'Ambrosio et al. | 250/361 R |
| 8,310,656 B2 * | 11/2012 | Zalewski | 356/29 |
| 2002/0057383 A1 * | 5/2002 | Iwamura | 348/734 |
| 2003/0057887 A1 * | 3/2003 | Dowling et al. | 315/291 |
| 2003/0093503 A1 * | 5/2003 | Yamaki et al. | 709/220 |
| 2003/0142204 A1 * | 7/2003 | Rus et al. | 348/65 |
| 2003/0189823 A1 * | 10/2003 | George et al. | 362/84 |
| 2004/0049344 A1 * | 3/2004 | Simon et al. | 701/301 |
| 2004/0234039 A1 * | 11/2004 | Karaus et al. | 378/196 |
| 2004/0257744 A1 * | 12/2004 | Bushko et al. | 361/179 |
| 2005/0088132 A1 * | 4/2005 | Curtis | 318/610 |
| 2005/0099824 A1 * | 5/2005 | Dowling et al. | 362/572 |
| 2005/0232467 A1 | 10/2005 | Mohri et al. | |
| 2005/0275626 A1 * | 12/2005 | Mueller et al. | 345/156 |
| 2005/0277096 A1 * | 12/2005 | Hendrickson et al. | 434/262 |
| 2006/0104479 A1 * | 5/2006 | Bonch-Osmolovskiy et al. | 382/103 |
| 2006/0153430 A1 * | 7/2006 | Canzler et al. | 382/118 |
| 2006/0155547 A1 * | 7/2006 | Browne et al. | 704/275 |
| 2007/0014567 A1 * | 1/2007 | Rossner et al. | 396/429 |
| 2008/0080789 A1 * | 4/2008 | Marks et al. | 382/296 |
| 2008/0088478 A1 * | 4/2008 | Shillman et al. | 340/928 |
| 2008/0192483 A1 * | 8/2008 | Mangiardi | 362/319 |
| 2008/0242993 A1 | 10/2008 | Shin | |
| 2008/0269596 A1 * | 10/2008 | Revie et al. | 600/424 |
| 2008/0285820 A1 | 11/2008 | Voelker | |
| 2009/0312101 A1 * | 12/2009 | Pope | 463/36 |
| 2010/0231421 A1 * | 9/2010 | Rawls-Meehan | 341/20 |
| 2011/0025818 A1 * | 2/2011 | Gallmeier et al. | 348/14.07 |
| 2011/0118898 A1 * | 5/2011 | Fu et al. | 701/1 |
| 2011/0154569 A1 * | 6/2011 | Wiggers et al. | 5/81.1 R |

FOREIGN PATENT DOCUMENTS

| | | |
|---|---|---|
| DE | 4201934 A1 | 7/1993 |
| DE | 19803494 A1 | 8/1999 |
| DE | 19811984 A1 | 9/1999 |
| DE | 19845027 A1 | 4/2000 |
| DE | 20001134 U1 | 5/2000 |
| DE | 19845028 A1 | 6/2000 |
| DE | 202007007054 U1 | 7/2007 |
| DE | 102008019191 A1 | 10/2009 |
| EP | 1408443 A1 | 4/2004 |
| EP | 1728482 A1 | 12/2006 |
| EP | 2215987 A1 | 8/2010 |
| WO | 0069354 A1 | 11/2000 |
| WO | 2007054367 A1 | 5/2007 |
| WO | 2008042219 A2 | 4/2008 |

OTHER PUBLICATIONS

European Search Report; Application No. EP10008373.2; Dec. 2, 2010; 6 pages.

* cited by examiner

CONTROL SYSTEM AND METHOD TO OPERATE AN OPERATING ROOM LAMP

CROSS-REFERENCE TO RELATED APPLICATIONS

The present application claims priority of German patent application No. 10 2009 037 316.0 filed on Aug. 14, 2009.

FIELD OF THE INVENTION

The present invention relates to a control system for an operating room lamp, a method to operate an operating room lamp, an operating room lamp, a computer program and a control device.

BACKGROUND OF THE INVENTION

Many diagnostic or therapeutic activities require or are based on a precise optical capture of a surgical site or of another area by medical personnel. For this purpose, bright, non-reflecting lighting is a requirement. This applies for instance to invasive or micro-invasive operations with therapeutic and/or diagnostic aims, to dermatological examinations and to dental and orthodontic examinations and operations.

Because as a rule the room light or ambient light is not sufficient for optimal illumination, lamps are used that are referred to hereinafter as operating room lamps, regardless of their intended application site within an operating room or in another place. The present invention relates, however, to operating room lamps in particular that are foreseen for use within an operating room because specific problems arise there with particular frequency and in unusual ways and thus led to the present invention, and because advantages of the present invention assume special importance there.

Therefore the following discussion focuses in particular on the situation in the operating room.

For optimum lighting, one or more operating room lamps are manually directed to the surgical site before the procedure takes place. Readjustment is made as necessary during the operation. For this purpose a sterile grip is positioned on each operating room lamp.

In DE 198 11 984 A1 a signal transmission network is described to which video cameras, remote-controlled operation room lamps, and control devices are connected.

WO 2007/054367 A1 presents an operating room lighting system with several lamps each with a control device. The control devices of the lamps communicate with one another via data interfaces and data lines.

DE 42 01 934 A1 proposes the control system of a data processing system using hand gestures.

In DE 200 01 134 U1 an operating room system is described that includes a projection surface for projecting operational elements onto a projection surface and a detection device for recognizing the movement of a finger on the projection surface.

DE 10 2008 019 191 A1 describes an apparatus for uniform illumination of a surgical site. A video camera captures an image of the surgical site. Individual lighting elements of an operating room light are switched on in order to achieve uniform lighting.

In EP 1 728 482 A1 a self-adjusting operation lamp system is described. Rotation point motors are provided in joints of an arm of a movable holder of an operating room lamp. Images from a video camera are used to control or regulate the position of the lamp when the field of vision of the camera is restricted.

DE 198 45 028 A1 describes a magnetic resonance system that is controlled by gestures picked up by a video camera.

In DE 198 93 484 A1 an operating room lamp is presented with a miniature video camera installed in the hand grip of the lamp body. Image signals are transmitted along the arm of the operating room lamp.

In DE 20 2007 007 054 U1 a system with an operating room lamp and a video camera is described. Information on the selected color temperature of the operating room lamp is transmitted to the video camera for an automatic white balance.

US 2005/0232467 A1 describes a device for capturing a movement of an object, in particular a hand motion, by means of an inertial sensor and a video camera fastened to the inertial sensor to capture an image of the environment of the object.

In EP 1 408 443 A1 are described a method and a device for analyzing gestures of a person to control a media playback device by means of gesture recognition.

In WO 00/69354 A1 a controllable camera platform is described for applications in telemedicine. The controllable camera platform is intended to avoid collisions or contacts with medical equipment, operating room lamps, and medical personnel. In addition an algorithm is described for moving the camera when the view of the observed object is obstructed.

DE 1 097 382 describes an operating room lamp with a photoelectric control system to move the operating room light. For a displacement in one direction, two photocells are situated in the housing of the operating room lamps with magnifiers mounted downstream. An operator can control the operating room lamp with a light emitter that, for example, emits UV and/or modulated light. If the two photovoltaic cells receive different quantities of light from the light emitter, then a motor is controlled by the relay to feed the operating room lamp until both photovoltaic cells again receive equal quantities of light.

This operating room lamp has a series of disadvantages. One of these disadvantages consists for many applications in the fact that the light emitter must be operated manually.

SUMMARY OF THE INVENTION

It is an object of the present invention to provide an improved control system to control an operating room lamp by medical personnel, an improved method for operating an operating room lamp, an improved operating room lamp, an improved computer program, and an improved control device.

This object is achieved through the subjects of the independent claims.

Refinements are indicated in the dependent claims.

Various embodiments of the present invention are based on the idea of configuring an operating room lamp with a video camera to capture an image of a surgical site, an image signal output, and a control signal input in such a way that at least either a direction or an intensity or a spectral characteristic of the light or a size or shape of the area illuminated by the light, depending on a control signal, can be modified or by means of the control signal can be controlled. An image input of a control system is coupled with the image signal output of the operating room lamp, and a control signal output of the control system is coupled with the control signal input of the operating room lamp. The control system is configured to generate the control signal depending on the image signal and to emit it to the control signal output. An image of the surgical site is captured by the video camera and an image signal is emitted. The image signal transmitted by the video camera to a control system. Depending on the image signal, a control signal is emitted by the control system. In particular in this process, a position, a movement or a gesture of a hand area, especially of a hand of an operator or other medical personnel is captured by the image signal and continues in the emission of the control signal.

In particular with large-surface surgical sites, for example with accident victims, the present invention ensures a definite simplification and improvement of the handling. The medical personnel can to a greater extent concentrate on its actual task, since it is no longer required to concern itself with moving the operating room lamp. In particular the cone of light emitted from the operating room lamp follows the operator's activities or those of other medical personnel and/or is adapted by the control system to the surgical field with respect to its size and extension.

A control system to control an operating room lamp for emitting light—in particular for illuminating a surgical site—includes an image signal input to receive an image signal from a video camera for capturing an image of the surgical site and a control signal output for emitting a control signal to control at least either a direction or an intensity or a spectral characteristic of the light or a size or image of the area to be illuminated by the lamp to the operating room lamp. The control system is configured to recognize a hand area of medical personnel in an image signal received by the video camera and to generate the control signal depending on the image signal and to emit it to the control signal output.

The hand area of the medical personnel includes in particular a hand and an area of the body adjoining it, in particular a forearm, a glove, an armband, a sleeve, or another article of clothing. The control system can be configured to recognize the hand area on the basis of its shape, its color, or a marking on the hand, on the glove, on an armband, on a sleeve or on another location.

The control system is particularly configured, on the basis of the image signal, to recognize and to capture at least either a position or a movement or a gesture of a hand area of medical personnel or of a marking in the hand area of the medical personnel and to generate the control signal depending on the position or movement or gesture.

Depending on the expected application, the recognition of a marking on a hand area, in particular on a hand or arm, of the medical personnel by means of an object recognition integrated in the control system can be an option that is especially easy to achieve and especially robust in operation. For this purpose the marking is differentiated from other objects captured by the video camera, for example in its form, its reflective properties, through a fluorescence or in other manner.

Alternatively or in addition, the control system is configured to capture the position or positions of the medical personnel or of other bodily parts of the medical personnel. For example, the positions of the arms or head of an operator or of other medical personnel can be captured in order to generate the control signal on the basis of these positions in such a way as to prevent light generated by the operating room lamp from being switched off. For example, the operating room lamp is displaced depending on the position or positions of the heads and arms of the medical personnel. With an operating room lamp that includes several individual lamps, a possible alternate is to switch off individual lamps whose light is shadowed by medical personnel and to switch on other individual lamps in order to maintain the lighting capacity.

Alternatively or in addition, the control system can be configured to recognize the position and extent of the surgical site, in particular the borders of the surgical site, and to generate the control signal depending on the position or extent of the surgical site or on the position of its borders.

In addition, the control system can be configured to recognize the position or a movement or gesture of a hand area of medical personnel that is provided with a marking, on the basis of a sensor signal of a sensor adapted to the marking, and to generate the control signal depending on the position or movement or gesture ascertained by the sensor signal.

The control system can be configured to determine on the basis of the image signal whether a position of a hand movement of medical personnel lies in a predetermined area, in particular whether it lies within the surgical site, and to generate the control signal depending on whether the position of the hand area lies in the predetermined spatial area.

In addition, the control system can be configured to determine a speed of a hand area of medical personnel in order to determine whether the speed of the hand area of the medical personnel lies within a predetermined speed range and in order to generate the control signal depending on whether the speed of the hand area of the medical personnel lies in the predetermined speed range.

For example, the control system can be configured in such a way that the position, the movement, or a gesture of a hand of a medical staff member is ignored if simultaneously the position of the hand or the speed of the hand lies within a predetermined range.

The control system can in addition be configured to receive a positioning signal that indicates a position or a change in position of a movable operating table or of an object with which the operating room lamp can collide and to generate the control signal depending on the positioning signal.

This object can be, for example, an additional operating room lamp, a screen or an instrument carrier that is affixed rigidly or movably on the ceiling of the operating room or that stands on the operating room floor. The positioning signal can be a setpoint signal, which constitutes a desired terminal position or a change to be made in the position of the movable operating table or of the object and that is used for instance to control the operating table or the object, if the latter is movable. Alternatively or in addition, the positioning signal can be a status signal, which constitutes an actually existing position or an existing change in position of the movable operating tale or of the object. The control system is configured, for example, to receive the positioning signal via a bus or another signal line from a sensor or another device or from a storage device. The storage device and the control system can be located in a common housing. For example, the position of the object with which the operating room lamp can collide is filed in the storage device. The positioning signal can continue in the generation of the control signal in order, for example, to control a simultaneous repositioning of the operating room lamp in case of a change in position of the adjustable operating table or to avoid a collision of the operating room lamp with the object.

Alternatively or in addition to the recognition of a hand area, the control can be configured at least either to recognize a movement of a head, an expression of a face, or an eye movement by medical personnel and to generate the control signal depending on the movement of the head, the facial expression, or the eye movement.

In particular, the control system is configured to recognize a head in an image signal received by the video camera, to recognize a head movement, and to generate the control signal depending on the recognized movement of the head. For this purpose the control system identifies predetermined movement patterns as commands for controlling the operating room lamp.

Alternatively or in addition, the control system can be configured to recognize a face in an image signal received by the video camera, to recognize an expression of the face, and to generate the control signal depending on the recognized expression. For this purpose the control system identifies predetermined facial expression patterns as commands for controlling the operating room lamp.

Alternatively or in addition, the control system can be configured to recognize an eye or both eyes in an image signal received by the video camera, to recognize the direction of a glance, a change in glance direction, a blink or other eye movement, and to generate the control signal depending on the recognized eye movement. For this purpose the control system identifies predetermined eye movements as commands for controlling the operating room lamp.

To control the operating room lamp by means of eye movements, a graphical user interface (GUI) can be displayed on a screen or projected on a surface, which screen or surface lies in the angle of vision of the medical personnel. This graphical user interface can include operating knobs and buttons with which control functions are associated. These control functions include for example the dimming of the operating room lamp or one of the operating room lamps or of individual lamps in the operating room lamp or in general lighting ("brighter"/"darker"); changing in the position of the operating room lamp or of one of the operating room lamps or of an individual lamp in the operating room lamp ("left"/"right," "forward"/"back," "up/down"); changing in focusing or in the shape and/or size of the illuminated area ("larger"/"smaller," "narrower"/"wider," "longer"/"shorter"); changing in the color temperature of the operating room lamp and/or in the general lighting ("warmer"/"colder" or "lower"/"higher").

The control system is configured, for example, to recognize that the glance of the relevant medical personnel rests on a button and glides slowly upward or downward from there, or to recognize that the glance rests on a button, and simultaneously to recognize a blink, and to identify these eye movements with an actuation of the button, or to recognize that the dwell time of the glance on a button exceeds a first predetermined threshold value and/or falls below a second predetermined threshold value.

Alternatively or in addition to buttons, the graphical user interface can indicate a realistic or schematized image of the operating table and/or of the patient and/or of the surgical site. The control system is configured, for example, by eye movements to direct the light of the operating room lamp to a particular location, on the representation of which in the image the medical personnel's glance rests, or on the basis of an eye movement, which surrounds the area to be illuminated, to adjust the focusing of the operating room lamp.

An operating room lamp system includes a control system as described here and an operating room lamp to generate light, and thus the operating room lamp includes a video camera to capture an image of a surgical site and to generate an image signal, an image signal output to convey the image signal to a control system, and a control signal input to receive a control signal from the control system. The operating room lamp is configured to change at least either a direction or an intensity or a spectral characteristic of the light or a size or shape of the area illuminated by the light, depending on the control signal.

With the operating room lighting system, the operating room lamp at least can either be mounted on a track device or can include a number of individual lamps combined in an array or in another uniform or non-uniform manner.

An operating room lighting system includes an operating room lamp to generate light and a track device, so that the operating room lamp can move along the track device.

The operating room lamp can be of the kind described above; that is, it can in particular include a video camera. In addition, the operating room lighting system can include a control system as described above. The operating room lighting system can include several lamps, which are coupled with one another or can be moved independently of one another along the track device. The operating room lamp or lamps in particular are movable because of the control signals, which are emitted by the aforementioned control system.

The track device of the operating lighting system can be configured in such a way that the entire operating room lighting system forms a low structural height. Consequently the operating lighting system can also be installed in a low operating room, in which the use of a conventional lighting arm with several joints is a disadvantage, because the operating room lamp hangs too low and/or restricts the mobility of the medical staff. Also in an operating room with standard height a low structural height can be advantageous because the operating room lamp can be positioned at greater height and thus it disturbs the medical personnel less or not at all. In addition, further apparatuses such as image screens or other devices can be positioned more freely if the operating room lamp is placed at a greater height.

The track device includes in particular a simple track or two or more parallel tracks. A trolley device is positioned so that it can move on this track or these tracks. The trolley device is partly or completely mounted above the track or tracks. Alternatively, the trolley device can be positioned below the track or tracks and surrounding them partly or completely. The trolley device in particular is electrically powered in order to be moved along the track or tracks on the basis of a control signal.

The track or tracks can have a circular, elliptical, oval, essentially rectangular, U-shaped, L-shaped, or other shape in order to make possible a corresponding mobility of the operating table lamp. In particular the track device includes a first and a second parallel track, at a distance from one another, on which a third track mounted crosswise to the first and second tracks can move, in similar manner to a portal crane, so that the operating room lamp is movable along the third track.

The operating room lamp can be positioned on the trolley deice either rigidly or so that it can pivot around one or more pivot axes. In addition, the operating room lamp can be translationally movable with respect to the trolley device. For example, the operating room lamp is positioned to move along a track positioned rigidly or movably on the trolley device or on a pivotable arm.

With a method to operate an operating room lamp to generate light, in particular to illuminate a surgical site, an image of the surgical site is captured and an image signal is generated by a video camera, the image signal is transmitted from the video camera to a control system, a hand area of medical personnel is recognized, a control signal is generated depending on the image signal, and at least either a direction or an intensity or a spectral characteristic of the light or a size or shape of the area illuminated by the light is controlled by the control signal.

The hand area of the medical personnel includes in particular a hand or a body area connected with it, in particular a forearm, a glove, armband, sleeve, or other article of clothing. With the method the hand area can be recognized on the basis of its shape, its color, or a marking on the hand, on the glove, on a forearm, on a sleeve or on another area.

With the method, in addition, at least either a position or a movement or a gesture of a hand area of medical personnel or a marking in the hand area of the medical personnel can be determined on the basis of the image signal, where the control signal is generated depending on the position or movement or gesture of the hand area.

Depending on the expected application, the recognition of a marking in a hand area of the medical personnel by means of an algorithm for object recognition can be an option that is especially easy to recognize and especially robust in operation. For this purpose the marking is differentiated for instance in its form, in its reflexive characteristics, by a fluorescence or in another way from other objects captured by the video camera.

With the method, in addition, at least either a position or a movement or a gesture of a hand area bearing a marking can be determined by medical personnel on the basis of a sensor signal of a sensor adapted to the marking, where in addition the control signal is generated depending on the position or movement or gesture of the hand area of the medical personnel determined on the basis of the sensor signal.

It is also possible to determine whether the position of the hand area, in particular of the marking, lies in a predetermined spatial area, such that the control signal in addition is generated depending on whether the position of the hand area lies in the predetermined spatial area.

In addition, the speed of the hand area of the medical personnel can be determined, along with whether the speed lies within a predetermined speed range, such that the control signal is generated depending on whether the speed lies in the predetermined speed range.

For example, a position or a movement or a gesture of a hand area, in particular of a hand, of the medical personnel or of a marking in the hand area is ignored and has no influence on the generation of the control signal if the position of the hand area or of the marking lies outside the predetermined range or the hand area or the marking is moved too quickly.

With one of the aforementioned methods, in addition, a positioning signal can be captured that indicates a position or a change in the position of the movable operating table or of an object with which the operating table lamp can collide, such that the control signal is generated depending on the positioning signal.

The positioning signal can be received by a bus or another signal line from a sensor or another device or from a storage facility, such that the storage facility and the control system can be located in a common housing. As shown above in connection with the control system, this object is for example an additional operating room lamp, a screen, or an instrument platform, which is mounted rigidly or movably on the ceiling of the operating room or stands on the floor of the operating room. As also discussed above, the positioning signal can be a status symbol or a setpoint signal. Consequently, with a change in position of the movable operating table, a simultaneous readjustment of the operating room lamp can be controlled and/or a collision of the operating room lamp with another object can be prevented.

With one of the aforementioned methods, in addition, an identity of the medical personnel can be captured by means of the video camera or otherwise.

The identity of the medical personnel can be acquired, for instance, on the basis of a marking that can be captured electrically, magnetically, electromagnetically or by means of an ultrasound or of a transponder on a glove or armband of the medical personnel. For this purpose the marking is read out in particular by means of a corresponding sensor, for instance by means of an ultrasound sensor or an RFID sensor. The marking can, with corresponding configuration, be read out simultaneously or in alternation or selectively by other means (electrically, magnetically, electromagnetically, by ultrasound, and so on). Through the non-optical capture of the marking, in place of the capture of the identity of the medical personnel or in addition to it, a determination of the position of the marking can also be made.

After acquiring the identity of the medical personnel, they can be registered in an operating room system.

On the basis of the registration, settings for instruments in the operating room as preferred by medical personnel, for instance, can be entered or an entry can be made in a log.

A control device to control an operating room lamp includes a marking that can be captured electromagnetically or by ultrasound and an attachment device to fasten the marking on a hand of medical personnel. The attachment device is, for instance, a glove or armband for medical personnel. The marking includes, for instance, a light source emitting in infrared, in the visible range or in UV, an ultrasound source, a transponder, a reflector for electromagnetic radiation or a fluorescent dye.

In all embodiments, the image signals generated by the video camera and transmitted to the control system and the control signals generated by the control system and transmitted to the operating room lamp are in each case, for instance, electric or optical signals, which are transmitted by corresponding lines.

In all described embodiments, the video camera can be configured to provide a black-and-white image or a color image. The video camera can be sensitive merely in the spectral range visible to the human eye. Alternatively or in addition, the video camera can be sensitive in the near or far infrared range. In addition, the video camera can be a stereo camera or can include two individual cameras that are directed from different shooting positions essentially to the same photographic field. In addition, the camera can be a time-of-flight camera, which determines the distance of the camera from the object or makes possible a determination of this distance on the basis of the duration of a light pulse from a light source to the object and from the object to the camera.

The operating room lamp is, for instance, an operating room lamp with an arm that can move in several degrees of freedom. This arm, similarly to a robot arm as used in numerous variants in industrial manufacturing, can be mechanically adjusted in its degrees of freedom. Alternatively, the operating room lamp includes one or more arrays of light diodes or other light sources or individual lamps with directed emission, which are positioned close to the ceiling of the operating room or inserted into the ceiling. These arrays or individual light sources or groups of light sources within an array are in particular individually switchable and/or dimmable or controllable in their light emission, in order to control the direction from which light is cast onto the surgical site. In addition, for each individual light source or for each group of light sources, the focusing or divergence of the light bundle emitting from an individual light source or from a group of light sources can be adjustable. In addition, the arrays or individual light sources or groups of light sources can be movable, in particular pivotable, around one, two, or more axes by means of servomotors.

The present invention can be implemented as a method or as a computer program with program code to execute or control such a method when the computer program runs on a computer or a processor. In addition, the invention can be implemented as a computer program product with a program code to execute one of the cited methods that is stored on a mechanically readable carrier (for example an ROM, PROM, EPROM, EEPROM or Flash storage device, a CD-ROM, DVD, HD-DVD, Blue-Ray disk, diskette or hard disk) or in the form of firmware when the computer program product runs on a computer or processor. In addition, the present invention can be implemented as a digital storage medium (for example, ROM, PROM, EPROM, EEPROM, or Flash storage device, CD-ROM, DVD, HD-DVD, Blue Ray disk, diskette or hard disk) with electronically readable control signals that can interact with a programmable computer or processor system in such a way that one of the described methods is executed.

In addition, the present invention can be implemented as a control system, so that the control system is configured to execute one of the described methods or so that the control system includes a computer program, a computer program product, or a digital storage medium as described in the preceding paragraph.

BRIEF DESCRIPTION OF THE DRAWINGS

Hereafter embodiments are explained more closely with reference to the appended drawings, as follows.

DETAILED DESCRIPTION OF THE INVENTION

Figure 1:
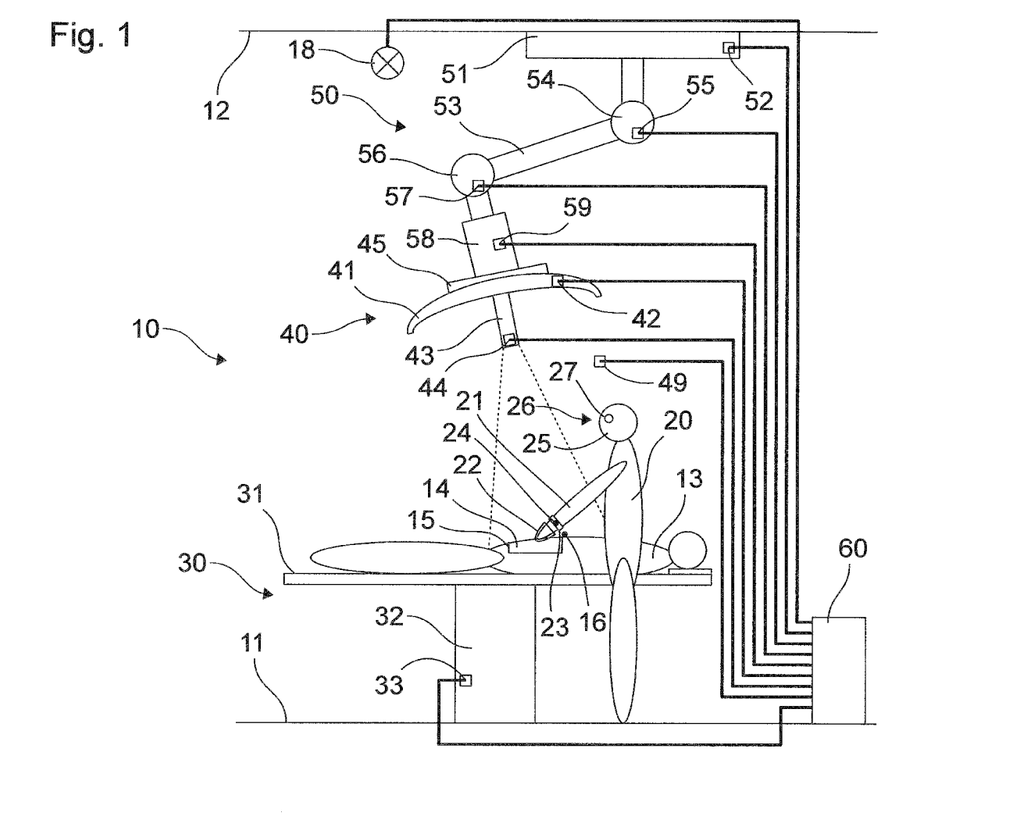
FIG. 1 shows a schematic depiction of an operating room.

FIG. 1 shows an operating room 10 with a floor 11 and a ceiling 12. A patient 13 is shown marked with a surgical site 14 with a border 15. The surgical site 14 and its border 15 are defined, for example, by the type of diagnostic or therapeutic procedure. One or more markings 16, which can be captured electrically, magnetically, electro-magnetically or by ultra-sound, can be provided on the border 15 of the surgical site 14. The operating room 10 includes a general lighting 18, which is positioned in particular on the ceiling 12 of the operating room 10 and is configured to provide a uniform brightness in the entire operating room 10.

An operator 20 or other medical personnel wears a glove 22 on the distal end of his or her arm 21 or on the hand and/or an armband 23 with one or more markings 24 that can be captured electrically, magnetically, electromagnetically, or by ultrasound.

The patient 13 lies on an operating table 30 with a lying surface 31. By means of an adjuster motor 32, the lying surface 31 can be adjusted, for example, in its height above the floor 11 and in its inclination with respect to the floor 11. The adjuster motor 32 of the operating table 30 includes a control signal input 33.

Positioned above the surgical site 14 is an operating room lamp 40 with a reflector 41 and a control signal input 42. The operating room lamp can include a single lamp or a number of individual lamps. Individual lamps of the operating room lamp 40 each include, for example, one or more light diodes. For instance, the individual lamps each include one or more RGB light diodes, RGBW light diodes, white light diodes based on fluorescence or phosphorescence, individual red, green and blue light diodes, or light diodes in secondary colors. Each individual light diode can be an inorganic or an organic light diode (also designated as OLED).

Each individual lamp can include a reflector, which can be movable in order to shift the direction and the focusing or the divergence of the light bundle emitting from the individual lamp. Individual lamps can be configured to provide light of varying spectral characteristics, in particular light of varying wavelength ranges or colors or varying color temperatures. Light provided by the operating room lamp can be adjusted with respect to its direction and the extent of the illuminated range by switching individual lamps on or off or by joint or independent pivoting of individual lamps to the place and extent of the surgical site 14.

The operating room lamp 40 includes a video camera 43 with an image signal output 44. The reflector 41 and video camera 43 of the operating room lamp 40 are connected with a suspension device 50 by a mechanical adapter or a support system 45. In addition, one or more sensors 49, for example ultrasound sensors or RFID sensors, are positioned in the operating room 10.

The suspension device 50 of the operating room lamp 40 includes a ceiling platform 51 that is attached to the ceiling 12 of the operating room 10 and has a control signal input 52. A lamp arm 53 connects the support system 45 with the ceiling platform 51. Provided on or in the lamp arm 53 are a first joint 54 with a control signal input 55 and a second joint 56 with a control signal input 57. On the end facing the reflector 41, the lamp arm 53 comprises a hexapod 58 with a control signal input 59, which is mechanically connected with the support system 45.

The hexapod 58 comprises six legs, each connecting a first component with a facing second component of the lamp arm 53. Several or all of the legs are mechanically length-adjustable. Each leg is jointed and fastened at an attachment point on the first component and at an attachment point on the second component. The attachment points are positioned on the two components in such a way that the relative arrangement and alignment of the two components are clearly determined by the lengths of the legs.

The position of the operating room lamp 40, in particular of the reflector 41 and of the video camera 43, and their light direction can be adjusted by mechanical or servomechanical drives of the joints 54, 56 of the hexapod 58 and in the ceiling platform 51. For example, a mechanical or servomechanical drive in or on the ceiling platform 51 allows a rotation of the suspension 50 around a vertical axis. Adjustability around one or two axes each on each of the joints 54, 56—optionally a telescopic adjustability of the lamp arm 53, not shown in FIG. 1, or other joints—and the hexapod 58 allow a sliding of the reflector 41 and of the video camera 43 in all dimensions and a nearly unlimited alignment of the reflector 41 and video camera 43. Here, rotatability around a vertical axis on the ceiling platform 51, the joints 54, 56, and the optional telescopic adjustability of the lamp arm 53 allow a large-scale displacement of reflector 41 and video camera 43. The hexapod 58, first of all, allows rotation and pivoting around several axes and a small-scale displacement of the reflector 41 and video camera 43. In addition, the intensity, spectrum, and size of the light cone or of the area illuminated by it, and/or the shape of the light cone can be controlled by a control signal on the control signal input 42.

Although the ceiling platform 51, the joints 54, 56, and the hexapod 58 are shown each with its own control signal inputs 52, 55, 57, 59, alternatively a single control signal input can be provided on the entire operating room lamp 40 including the suspension 50. It can, in addition, be integrated with the control signal input 42 of the light source and/or the image signal output 44 of the video camera 43. The routing of the lines running between the control system 60 on the one hand and the image signal output 44 and control signal inputs 33, 52, 55, 57, 59 on the other hand can differ from the schematic depiction in FIG. 1. In particular, routing them inside the lamp arm 53 is advantageous for hygienic and other practical reasons.

A control system 60 is coupled with the general lighting 18 or a capacity supply or switching device for general lighting 18, with the control signal input 33 of the adjuster motor 32 of the operating table 30, with the control signal input 42 of the light source, with the image signal output 44 of the video camera 43, with the sensor 49, with the control signal input 52 on the ceiling platform 51, with the control signal input 55 on the first joint 54, with the control signal input 57 on the second joint 56, and with the control signal input 59 on the hexapod 58. This coupling, as shown in FIG. 1, can occur between lines running in star configuration between the control system 60 on the one hand and the control signal inputs or image signal outputs 33, 42, 44, 52, 55, 57, 59 on the other hand or by one or more busses, for example an SCB (Storz Communication Bus) or a CAN bus. A coupling by one or more bus systems reduces the number of required lines.

The video camera 43 can be configured to capture a monochromatic image or a black-and-white image or to capture images in several different spectral ranges or to capture a color image. The spectral sensitivity of the camera can be restricted to the range visible to the human eye or can be essentially restricted to this spectral range. Alternatively or in addition, the camera is sensitive in other spectral ranges, for instance in the near, medium and/or distant infrared.

The video camera 43 can be a stereo camera or can include two partial cameras whose photographing positions are different. Three-dimensional image information can be obtained from the differences between two images captured simultaneously by the partial cameras. In particular, distances of acquired objects can be determined by the stereo camera. Alternatively the camera 43 can be, for example, a time-of-flight camera, which allows a determination of three-dimensional image information from the durations of a brief light pulse.

Figure 2:
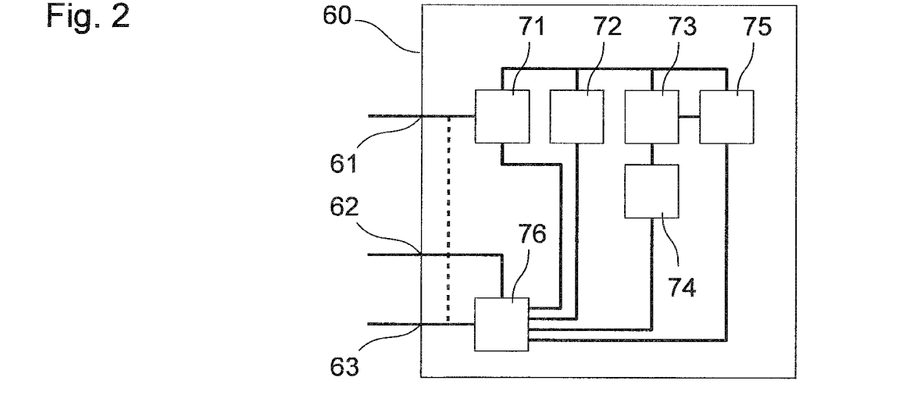
FIG. 2 shows a schematic depiction of a control system.

FIG. 2 shows a schematic depiction of a control system similar to the one presented above in FIG. 1. The control system 60 in FIG. 2 is distinguished from the aforementioned one in FIG. 2, however, by the number of inputs and outputs. The control system 60 in FIG. 2 comprises an image signal input 61, a positioning signal input 62, and a control signal output 63. The image signal input 61 is configured to be coupled with the image signal output 44 of the camera 43 of the operating room light 40. The positioning signal input 62 is configured to be coupled parallel to the control signal input 33 of the operating table 30 and like it, to receive a positioning signal to control the operating table 30. Alternatively or in addition, the positioning input 62 is configured to receive a positioning signal that depicts a position or a change in position of an object with which the operating room lamp 40 can collide. The control signal output 63 is configured to be coupled with one or more control signal inputs 42, 52, 55, 57, 59 of the operating room lamp 40.

The interrupted line 64 indicates that the control system 60 alternatively only comprises one or two signal inputs and outputs 61, 62 or 63, which integrate the functions of the image signal input 61 and/or of the positioning signal input 62 and/or of the control signal output 63. One or two such integrated signal inputs and outputs assume the tasks both of the image signal input 61 and of the positioning signal input 62 and of the control signal output 63. These one or two signal inputs and outputs, in particular, are then each configured to be coupled with a bus (for example, SCB or CAN), by which all control signals or all control signals and all image signals are transmitted. In the following, however, reference is made again to the image signal input 61, the positioning signal input 62 and the control signal output 63. However, the functionality thereby described is independent of the number and type of inputs and outputs. The transmission of all signals by a single bus or few bus systems, however, is advantageous in many cases.

The control system 60 includes a first device 71, a second device 72, a third device 73, a fourth device 74, a fifth device 75 and a sixth device 76. The first device 71 is coupled with the image signal input 61, the second device 72, the third device 73, the fifth device 75 and the sixth device 76. The second device 72 is coupled with the first device 71 and the sixth device 76. The third device 73 is coupled with the first device 71, the fourth device 74 and the fifth device 75. The fourth device 74 is coupled with the third device 73 and the sixth device 76. The fifth device 75 is coupled with the first device 71, the third device 73 and the sixth device 76. The sixth device 76 is coupled with the positioning signal input 62 and the control signal output 63. A coupling thus contains in each case at least the possibility of a direct or indirect exchange of information or of a signal that depicts the information.

The first device 71 is configured for image recognition, in particular for the recognition of a hand of an operator or of a marking 24, 16 on a glove 22, an armband 23 or an outline 15 of a surgical site 14. The first device 71 in addition is configured to determine the position of the hand or of the marking 16, 24. The second device 72 is configured to determine whether the position determined by the first device 71 lies inside a predetermined range. The third device 73 is configured to ascertain a speed of the hand or of the marking 16, 24. The fourth device 74 is configured to determine whether the speed ascertained by the third device 73 lies within a predetermined range. The fifth device 75 is configured to recognize a gesture by the hand of the operator or by the marking 24. The sixth device 76 is configured to generate a control signal to the control system of the operating room lamp 40, optionally to generate a control signal for the general lighting 18 and optionally to generate a control signal to control the operating table 30.

The first device 71, or a second device not shown in FIG. 2, can in addition be configured to receive sensor signals from the sensor or sensors 49 and on the basis of these sensor signals to determine the identity of the marking 24 and of the operator and/or the positions of the markings 24, 16. These sensors 49 are attuned to the markings 24, 16, for instance ultrasound sensors or RFID sensors.

Instead of the positioning signal input 62 or in addition to it, a positioning signal output can be provided by which the control system 60 is coupled with the control signal input 33 of the operating table 30 and/or with control signal inputs from one or more objects with which the operating room lamp 40 can collide. In this case the sixth device 76 is also configured to generate a positioning signal for the operating table 30 or the object.

The first device 71 receives via the image signal input 61 an image signal and evaluates said signal, for instance with respect to the momentary arrangement of individually predetermined image elements. These image elements include for instance the hand of the operator 20 or parts of the same or one or more markings 16, 24. This marking is distinguished and can be bordered off from other objects, for instance, on the basis of its color, its reflectance, its shape or a time modulation of its reflectance or of its illumination. The second device 72, the third device 73, the fifth device 75 and the sixth device 76 receive the position or positions and optionally additional information on the arrangement and alignment or orientation of the predetermined characteristic or characteristics in the image acquired by the video camera 43.

Alternatively or in addition, the first device 71 or a device not shown in FIG. 2 receives sensor signals from the sensor or sensors 49 (for example, ultrasound sensors or RFID sensors). The first device 71 or a device not shown in FIG. 2 evaluates these sensor signals with respect to the identity or identities of the markings 24, 16 and/or to the positions or orientations of the markings 24, 16.

The second device 72 compares the position or positions with a predetermined area, for example with the surgical site 14 and its border 15. This border 15 of the surgical site can be marked by one or more markings 16. Alternatively the border 15 of the surgical site 14 is recognized and localized by the first device 71 or by the second device 72, for example by means of image recognition or pattern recognition software.

The third device 73 ascertains one or more speeds of the observed characteristic or characteristics 16, 24, for example from the comparison of positions that are determined by the first device 71 on the basis of several successively acquired images. The fourth device 74 compares the speed ascertained by the third device 73 with one or more predetermined areas. For example, the third device 73 compares the amount and/or one or more Cartesian components of the speed individually with an upper limit. The fifth device 75 analyzes the positions determined by the first device 71 and the speeds determined by the third device 73 and identifies one or more gestures of the operator's 20 hand.

The sixth device 76 receives from the first device 71 the position or positions and optionally the alignment of relevant characteristics in the image acquired by the video camera 43. Alternatively or in addition, the sixth device 76 receives from the second device 72 information on whether the speed determined by the third device 73 or certain speeds lie within one or more predetermined areas. Alternatively or in addition, the sixth device 76 receives from the fifth device 75 information on gestures executed by the operator's 20 hand. Alternatively or in addition, the sixth device 76 receives a positioning signal that constitutes a position or a change in position of the operating table 30 or of an object with which the operating room lamp 40 can collide.

On the basis of this information the sixth device 76 generates one or more control signals for the drives in or on the ceiling platform 51, of the joints 54, 56 and hexapod 58. The sixth device 76 generates the control signal or signals in such a way that the light generated by the operating room lamp 40 or the light cone, even during a movement of the operating table 40 and of the patient 13 in the operating room 10, is directed to the surgical site 14 and completely and uniformly illuminates said site. Alternatively or in addition, the sixth device 76 generates the control signal or signals in such a way that the light generated by the operating room lamp 40 always illuminates the operator's 20 hand or a marking 24 on the operator's 20 hand and its surroundings. Alternatively or in addition, the sixth device 76 generates the control signal or signals in such a way that the operator 20 can influence the direction, the intensity, a spectral characteristic of the light generated by the operating room lamp 40 or a shape of the area illuminated by the light, with predetermined gestures that he or she executes with one or both hands. Alternatively or in addition, the sixth device 76 generates the control signal or signals in such a way that movements or gestures of the operator's 20 hand are not taken into account in the control of the operating room lamp 40 if they are executed outside a predetermined area, for example outside the surgical site 14, or are executed at too great a speed.

Alternatively or in addition, the sixth device 76 generates a control signal for the control signal input 42 by which, for instance, the intensity, spectral characteristics, size or shape of the light cone or of the area illuminated by the operating room lamp 40 is controlled.

Alternatively the sixth device 76 is configured to generate a positioning signal for the operating table 30 or for an object with which the operating room lamp can collide. Independently of whether the control system is configured to receive or to generate and send a positioning signal, the sixth device 76 is configured to generate the control signal (and if applicable the positioning signal) in such a way that the operating room lamp does not in any case collide with the object.

The first device 71 or another device, not shown in FIG. 2, of the control system 60 can be configured to recognize, in addition to the recognition of a hand of an operator 20, an arm 21, a head 25, or one or more other body parts of medical personnel and to determine the positions of these body parts or the positions of medical personnel. In this case the control system 60 and the devices 71, 72, 73, 74, 75, 76 that constitute it can be configured in such a way that the control signal is generated depending on the positions of the medical personnel or of arms 21, heads 25 or other body parts of the medical personnel. In particular, the control system 60 is configured to generate the control signal in such a way as to prevent shadowing by arms, heads, or upper bodies of medical personnel of the light generated by the operating room lamp 40.

In addition, the control system 60 can be configured to receive an image signal of a video camera directed at the head 25 of the operator 20 or other medical personnel and to recognize in the image signal the head 25 of the operator 20 and other medical personnel and a movement of the head 25 and to control the operating room lamp 40 depending on a movement of the head 25 recognized as a control command. Alternatively or in addition, the control system 60 can be configured to recognize an eye 27 or both eyes of the medical personnel 20, a direction of a glance, a change in glance direction, a blink and/or other eye movement and to control the operating room lamp 40 depending on an eye movement recognized as a control command. Alternatively or in addition, the control system 60 can be configured to recognize an expression of the face 26 of the operator and to control the operating room lamp 40 depending on an expression recognized as a control command.

In addition, the control system 60 can be configured to control the operating room light 40 in such a way as to avoid dazzling of medical personnel directly by the operating room lamp 40 or by reflections on medical instruments.

If the operating room lamp includes several individual lamps, the control system 60 can be configured to switch off individual lamps whose light may be shadowed or to reduce their output, and simultaneously to switch on other individual lamps as compensation. In addition, the control system 60 can be configured to correct the direction and/or the focusing or divergence of the light provided by individual lamps by adjusting reflectors of the individual lamps.

The devices 71, 72, 73, 74, 75, 76 of the control system 60 can be separate devices as shown in FIG. 2. Alternatively the functionalities of several devices 71, 72, 73, 74, 75, 76 are integrated in one device. In addition, the functionalities of all or of some of the devices 71, 72, 73, 74, 75, 76 can be realized by computer programs, functions, partial programs or threads, which run in one or more processors.

Figure 3:
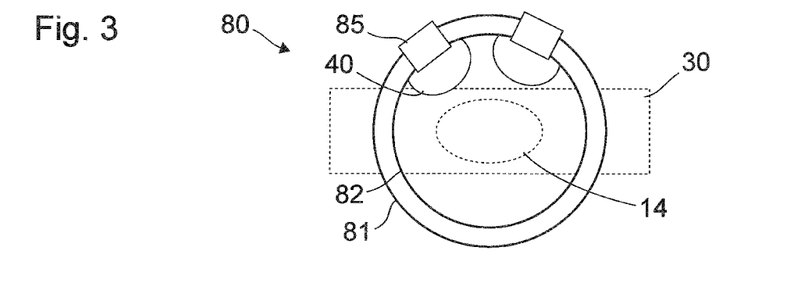
FIG. 3 shows a schematic depiction of operating room lamps on a track device.
Figure 4:
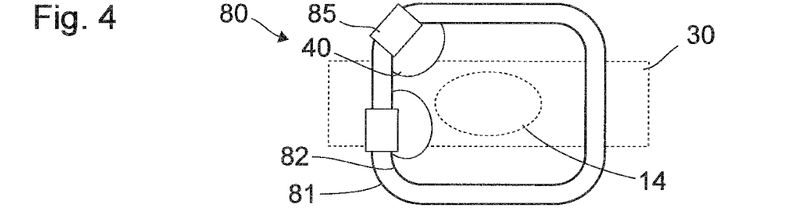
FIG. 4 shows a schematic depiction of operating room lamps on a track device.
Figure 5:
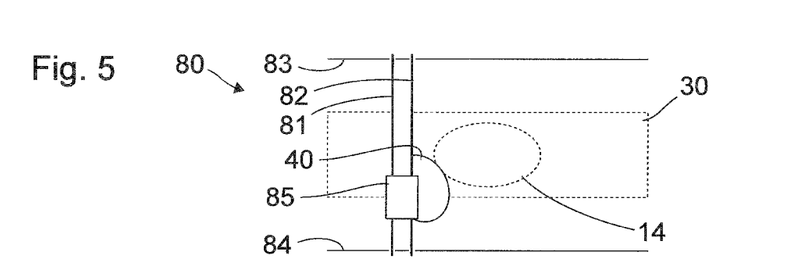
FIG. 5 shows a schematic depiction of an operating room lamp on a track device.

FIGS. 3 to 5 show schematic depictions of three different embodiments of a track device 80, each with one or more operating room lamps 40. The illustrated track devices are alternatives to the suspension of an operating room lamp on an arm with several joints, as presented above with reference to FIG. 1. In addition, the suspension illustrated in FIG. 1 and the track devices illustrated in FIGS. 3 through 5 can supplement one another or be combined with one another. In each of FIGS. 3 through 5, an overhead view is shown, so that the plane of projection is parallel to the operating room floor. The operating table 30 and the surgical site 14 that is to be illuminated are indicated with a broken line.

Figure 6:
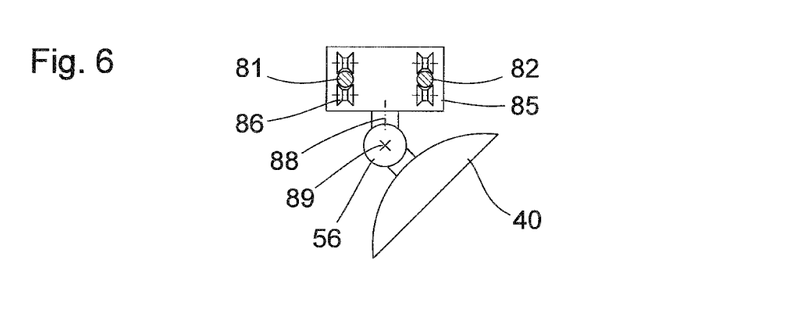
FIG. 6 shows a schematic depiction of an operating room lamp on a track device.

In the embodiment illustrated in FIG. 3 the track device 80 includes a first track 81 and a second track 82, positioned parallel to one another. Both the first track 81 and the second track 82 are circular in shape. The tracks 81, 82 are positioned concentrically in one plane. One, two or more trolley devices 85 can be moved along the tracks 81, 82, in particular by electric motors. The track devices 85 can each surround both tracks 81, 82 in order to prevent them from tipping over and falling down from the tracks 81, 82 from the impact of a force or moment on the trolley device 85.

An operating room lamp 40 is positioned on every trolley device 85. In particular the operating room lamp 40 is positioned in each case under the trolley device 85. An embodiment of a trolley device 85 is described more closely below with reference to FIG. 6.

The two trolley devices 85 with the operating lamps 40 mounted on them can be moved along the tracks, in particular independently of one another. To prevent a collision of the trolley devices 85 or of the operating room lamps 40, the control system 60 presented above with reference to FIGS. 1 and 2 can comprise a collision prevention device. Alternatively a collision prevention algorithm can be contained in software of the control system 60. In addition, a collision between the trolley devices 85 or the operating room lamps 40 can be prevented by means of proximity sensors or other devices on the trolley devices 85 or on the operating room lamps 40. Alternatively, consequences of a collision are avoided or reduced by means of impact-absorbing elements.

An advantage of the circular shape of the tracks 81, 82 shown in FIG. 3 is that the operating room lamp 40 or lamps 40 can be conducted around the surgical site 14 in order to illuminate the surgical site 114 from any desired direction. Instead of a circular shape, the tracks 81, 82 can have any other shape, for example elliptical, U-shaped, straight or S-shaped. An elliptical shape for the tracks 81, 82 as opposed to a circular design can have the advantage that the elliptical form can be adapted to the typically lengthwise-elongated shape of the body of the patient lying on the operating table 30.

FIG. 4 shows a schematic depiction of an example in which the tracks essentially have a rectangular shape with rounded corners. This shape of the tracks 81, 82 requires—similarly as with an elliptical shape or an S-shape figure of the tracks, for example—a configuration of the trolley device 85 that allows adjustment to a varying curvature of the tracks 81, 82. An advantage of the rectangular form of the tracks 81, 82 shown in FIG. 4 can consist in lower manufacturing costs for straight tracks 81, 82 and those that are arch-shaped and only comprise one individual radius of curvature.

FIG. 5 shows a schematic depiction of an additional embodiment of a track device 80. A trolley device 85 with an operating room lamp 40 is positioned on a first track 81 and a second track 82. The first track 81 and the second track 82 are each positioned straight and parallel to one another. Ends of the first track 81 and of the second track 82 can be transported along a third track 83 and a fourth track 84. The third track 83 and the fourth track 84 are each positioned straight and parallel to one another. The first track 81 and the second track 82 are essentially positioned perpendicular to the third track 83 and to the fourth track 84.

The trolley device 85 and with it the operating room lamp 40 can be moved along the first track 81 and the second track 82, in particularly by electric motor. Independently of that, the first track 81 and the second track 82 can be driven along the third track 83 and the fourth track 84, in particular by electric motor. Consequently the operating room lamp can be positioned as desired within a rectangular area whose dimensions are given essentially by the lengths of the tracks 81, 82, 83, 84. This allows the operating room lamp to be positioned optimally for many application cases.

Departing from the depiction in FIG. 5, several operating room lamps 40 can each be provided on a trolley device 85 that can be positioned independently of one another or largely independent of one another. In particular, for each trolley device 85, one particular pair of tracks 81, 82 are provided that can be driven along the third track 83 and the fourth track 84.

FIG. 6 shows a schematic depiction of a trolley device 85 on a first track 81 and a second track 82, as shown for example above with reference to FIGS. 3 through 5. The plane of projection of FIG. 6 is perpendicular to the planes of projection of FIGS. 3 through 5. In the example shown in FIG. 6, the tracks 81, 82 each have a circular-shaped or essentially circular-shaped cross-section. The trolley device 85 is run on the tracks 81, 82 and can be driven along them by means of several running wheels 86.

The trolley device 85 completely surrounds the tracks 81, 82. Running wheels 86 are positioned both above and below the tracks 81, 82. By this means the trolley device 85, even with the impact of forces or moments, cannot be lifted off the tracks 81, 82 or fall down. The trolley device 85 can comprise a drive device, which is not shown in FIG. 6. In particular, the trolley device 85 can comprise one or more electric motors or a linear drive.

The trolley device 85 is jointedly connected with an operating room light by a joint 56. The operating room lamp can pivot around a first pivot axis 88, which is parallel to the plane of projection of FIG. 6, and around a second pivot axis 89. The second pivot axis 89 is perpendicular to the first pivot axis 88, rotates with the operating room lamp 40 around the first pivot axis 88, and is perpendicular to the plane of projection of FIG. 6 in the position of the operating room lamp 40 shown in FIG. 6.

The movability of the trolley device 85 with the operating room lamp 40 along the first track 81 and the second track 82, the possible movability of the first track 81 and second track 82 along the third track 83 and fourth track 84, and the pivotability of the operating room lamp around the first pivot axis 88 and the second pivot axis 89 make possible a wide choice of positions and orientation for the operating room lamp 40. Consequently the operating room lamp 40 or several operating room lamps 40 can be positioned and aligned in many or all application cases in such a way that the surgical site 14 is optimally illuminated.

In all examples and variants shown in FIGS. 3 through 6, instead of two parallel tracks it is possible to provide only one track or three or more parallel tracks. The cross-sections of the track or tracks are, for example, circular, elliptical, rectangular, T-shaped, L-shaped, or I-shaped.

Figure 7:
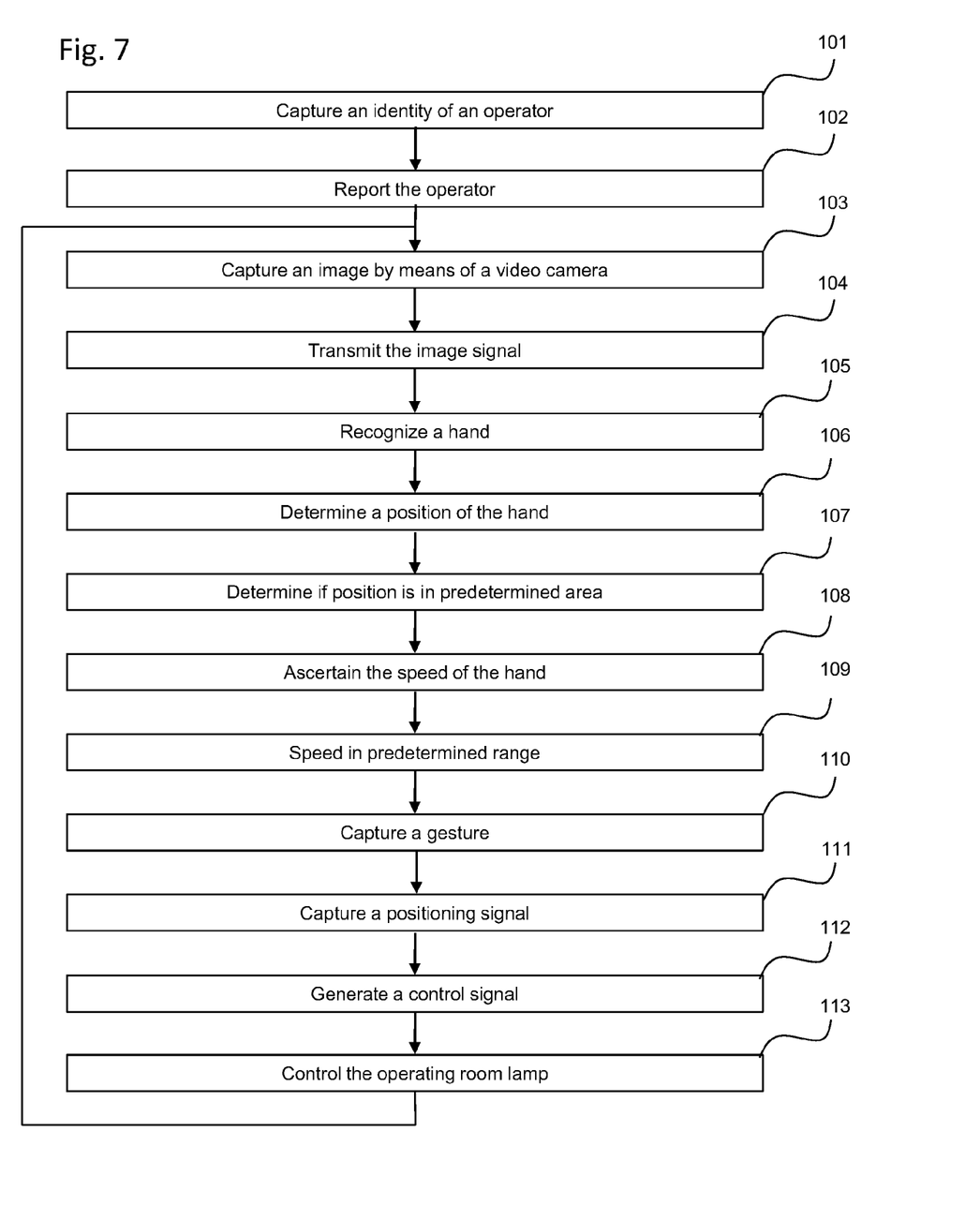
FIG. 7 shows a flow diagram of a method to operate an operating room lamp.

FIG. 7 shows a schematic flow diagram of a method to operate an operating room lamp to generate light. Although the method can also be performed with appliances that differ from those shown above in FIGS. 1 and 2, hereafter reference numbers from FIGS. 1 and 2 are used in order to facilitate clarity.

In a first step 101, an identity of the operator 20 is captured. This is done for example on the basis of a shape, a color, a reflectance, or a time modulation of a marking that can be acquired optically (in the infrared, visible, or ultraviolet spectral range) on a glove 22 or armband 23 of the operator 20 by a video camera 43 in the operating room lamp 40. Alternatively or in addition, the identification occurs by a transponder (for example, an RFID transponder) on or in the glove 22 or armband 23 of the operator 20 or in another way. In a second step 102 the operator 20 is announced in an operating room system, for example to generate a corresponding entry in a log, to make adjustments to devices in the operating room 10 as preferred by the operator 20, or to load parameters that are used to recognize gestures of the operator.

In a third step 103, by means of the video camera 43 of the operating room lamp 40, an image is acquired of the surgical site 14 and of the hand of the operator 20 with the glove 22 and/or the armband 23 and a marking 24 thereon. The video camera 43 generates an image signal, which in a fourth step 104 is transmitted by the camera 43 to a control system 60. The image signal is, for example, an analog or digital signal. With a transmission by a bus (for example, SCB or CAN), the transmission of the image signal is made for example in packets.

In a fifth step 105 the hand of the operator 20 is recognized, for example on the basis of its color or shape or of the marking 24 on the armband 23 or glove 22 of the operator 20. For this purpose, image recognition software is used, for example. In a sixth step 106, which can be integrated with the fifth step 105, a position of the hand is determined. This is, for example, a position relative to the image acquired by the video camera 43 or its borders 15 or a position in a fixed coordinate system in the operating room 10.

In determining the position of the hand in the sixth step 106, alternatively or in addition to the image signals of the camera 43, sensor signals can be used from one or more additional sensors 49. These sensors 49 are adapted to the marking 24, for example ultrasound sensors or RFID sensors.

In a seventh step 107, a determination is made whether the position determined in the sixth step 106 lies in a predetermined position range. In an eighth step 108 a speed of the hand of the operator 20 is determined, for example by comparing the positions of the hand that were determined at various points in time on the basis of several images. A ninth step 109 serves to determine whether the speed ascertained in the eighth step 108 lies in a predetermined speed range.

In a tenth step 110 a gesture executed by the hand of the operator 20 is captured, for example by comparing the positions and speeds of the hand that were determined or ascertained at various points in time. Gestures are, for instance, linearly oscillating or circling motions with determined direction or rotation direction like forming a fist, spreading one or more fingers, or executing predetermined movements of both hands in relation to one another.

In an eleventh step 111 one or more positioning signals are captured that depict the intended or actual position or a change in the position of the operating table 30, of another operating table lamp, or of another object with which the operating table lamp 40 can collide.

In a twelfth step 112 one or more control signals are generated to control the direction, intensity or spectral characteristic of the light of the operating table lamp 40 or of a shape of the area illuminated by the light. The control signal or signals are generated depending on the position or positions determined in the sixth step 106, on the gesture captured in the tenth step 110, and on the positioning signal or signals captured in the eleventh step 111, as well as on whether the position or positions and the speed or speeds lie within the predetermined ranges. In a thirteenth step 113 the operating room lamp 40 is controlled by the control signal generated in the twelfth step 112.

The third step 103, fourth step 104, fifth step 105, sixth step 106, seventh step 107, eighth step 108, ninth step 109, tenth step 110, eleventh step 111, twelfth step 112 and the thirteenth step 113 can be repeated periodically or non-periodically and executed in part in a sequence that departs from the depiction in FIG. 7 or in part simultaneously. The method can be supplemented by additional steps not shown in FIG. 7 or can be modified by omitting individual steps shown in FIG. 7.

The invention claimed is:

1. A control system to control an operating room lamp to generate light, with:
    an image signal input to receive an image signal from a video camera capturing an image of a surgical site;
    a control signal output to transmit a control signal to the operating room lamp, the control signal depending on the image signal which is generated by the video camera, the control signal controlling at least one of a direction, an intensity or a spectral characteristic of the light, or a size or shape of an area illuminated by the light;
    where the control system is configured to recognize a hand area of medical personnel in the image signal captured by the video camera and to continuously generate the control signal depending on the image signal and transmit it to the control signal output.

2. The control system according to claim 1, wherein the control system is configured to recognize, on the basis of the image signal, at least one of a position or a movement or a gesture of a hand area of medical personnel or a marking in the hand area of the medical personnel, and to generate the control signal depending on the position or movement or gesture.

3. The control system according to claim 1, wherein the control system in addition is configured to determine on the basis of the image signal whether a position of a hand area of medical personnel lies in a predetermined spatial area, and in addition to generate the control signal depending on whether the position of the hand area lies in the predetermined spatial area.

4. The control system according to claim 1, wherein the control system in addition is configured to determine a speed of a hand area of medical personnel, to determine whether the speed of the hand area of the medical personnel lies in a predetermined speed range, and in addition to generate the control signal depending on whether the speed of the hand area of the medical personnel lies in a predetermined speed range.

5. The control system according to claim 1, wherein the control system is configured in addition to receive a positioning signal that depicts a position or a change in position of an adjustable operating table or of an object with which the operating room lamp can collide, and to generate the control signal depending on the positioning signal.

6. The control system according to claim 1, wherein the control system is configured in addition to recognize at least one of a movement of a head, a facial expression or an eye movement of medical personnel, and to generate the control signal depending on the at least one of the movement of the head, the facial expression or the eye movement.

7. An operating room light system with a control system according to claim 1 and with an operating room lamp to generate light, where the operating room lamp includes:
- a video camera to capture an image of a surgical site and to generate an image signal;
- an image signal output to transmit the image signal to a control system;
- a control signal input to receive a control signal from the control system;
- where the operating room lamp is configured to modify at least one of a direction or an intensity or a spectral characteristic of the light or a size or shape of the area illuminated by the light, depending on the control signal.

8. The operating room lamp system according to claim 7, wherein the operating room lamp is at least either positioned on a track device or includes a number of individual lamps that are positioned in an array or in a manner that is either uniform or non-uniform.

9. A method for operating an operating room lamp to generate light, with the following steps:
- capture an image of the surgical site and generate an image signal by means of a video camera;
- transmit the image signal from the video camera to a control system;
- recognize a hand movement of medical personnel in the image signal;
- generate continuously a control signal depending on the image signal, which is generated by the video camera, and transmit continuously the control signal from the control system to the operating room lamp; and
- control at least one of a direction, an intensity or a spectral characteristic of the light, or a size or shape of an area illuminated by the light by means of the control signal.

10. The method according to claim 9, in addition with the following step:
- determine at least one of a position or a movement or a gesture of a hand area of medical personnel or a marking on the hand area of the medical personnel on the basis of the image signal,
- where the control signal in addition is generated depending on the position or the movement or the gesture of the hand area of the medial personnel.

11. The method according to claim 9, in addition with the following step:
- determine whether the position of the hand area of the medical personnel lies in a predetermined spatial area,
- where the control signal in addition is generated depending on whether the position of the hand area lies in the predetermined spatial area.

12. The method according to claim 9, in addition with the following step:
- determine the speed of the hand area of the medical personnel;
- determine whether the speed of the hand area of the medical personnel (20) lies in a predetermined speed range,
- where the control signal in addition is generated depending on whether the speed of the hand area of the medical personnel lies in the predetermined speed range.

13. The method according to claim 9, in addition with the following step:
- capture a positioning signal that indicates a position or a change in the position of an operating table or of an object with which the operating room lamp can collide,
- where the control signal is generated depending on the positioning signal.

14. The method according to claim 9, in addition with the following step:
- capture an identity of the medical personnel by means of a video camera or sensor.

15. The method according to claim 14, in addition with the following step:
- report the medical personnel in an operating room system.

* * * * *